United States Patent
Bell et al.

(10) Patent No.: US 8,846,858 B2
(45) Date of Patent: Sep. 30, 2014

(54) METHOD FOR ALCOHOLYSIS OF POLYCARBONATE COMPOSITIONS CONTAINING FLAME RETARDANT OR ACRYLONITRILE-BUTADIENE-STYRENE

(71) Applicant: Saudi Basic Industries Corporation, Riyadh (SA)

(72) Inventors: Philip Wesley Bell, Mount Vernon, IN (US); Alexander Stanislaus, Bangalore (IN); Venkata Ramanarayanan Ganapathy Bhotla, Bangalore (IN); Rathinam Jothi Mahalingam, Bangalore (IN)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/723,425

(22) Filed: Dec. 21, 2012

(65) Prior Publication Data
US 2014/0179892 A1 Jun. 26, 2014

(51) Int. Cl.
| C08G 64/00 | (2006.01) |
| C08G 64/06 | (2006.01) |
| C08G 64/30 | (2006.01) |
| C07C 37/50 | (2006.01) |
| C07C 68/06 | (2006.01) |
| C08G 64/40 | (2006.01) |
| C08G 63/02 | (2006.01) |

(52) U.S. Cl.
CPC .............. *C07C 37/50* (2013.01); *C08G 64/06* (2013.01); *C08G 64/307* (2013.01); *C07C 68/06* (2013.01); *C08G 64/406* (2013.01)
USPC ........... 528/503; 524/480; 524/502; 524/611; 528/190; 528/196; 528/198

(58) Field of Classification Search
USPC ........... 524/480, 502, 611; 528/190, 196, 198
See application file for complete search history.

(56) References Cited

U.S. PATENT DOCUMENTS

| 4,154,775 A | 5/1979 | Axelrod et al. |
| 4,447,659 A | 5/1984 | Blewett |
| 5,045,122 A | 9/1991 | Tindall et al. |
| 5,266,716 A | 11/1993 | Buysch et al. |
| 5,350,839 A | 9/1994 | Asaka et al. |
| 5,391,802 A | 2/1995 | Buysch et al. |
| 5,440,066 A | 8/1995 | Buysch et al. |
| 6,787,632 B2 | 9/2004 | Phelps et al. |
| 6,887,968 B2 | 5/2005 | Hahnsen et al. |
| 7,094,917 B2 | 8/2006 | Ridinger et al. |
| 7,585,930 B2 | 9/2009 | Kitahara et al. |
| 2004/0054238 A1 | 3/2004 | Ban et al. |
| 2004/0127720 A1 | 7/2004 | Hedrick et al. |

FOREIGN PATENT DOCUMENTS

| EP | 1439158 A1 | 7/2004 |
| GB | 2043083 A | 10/1980 |

OTHER PUBLICATIONS

JP2001302844 A English Abstract; Date of Publication Oct. 31, 2001; 2 pages.
JP2003041049 A English Abstract; Date of Publication Feb. 13, 2003; 1 page.
JP2005343840 A English Abstract; Date of Publication Dec. 15, 2005; 2 pages.
Anonymous; "Polycarbonate Recycling"; Research Disclosure; Sep. 1997; 2 pages.
European Search Report for International Application No. 12382521.8; Date of Completion May 14, 2013; 6 pages.
DE 4324778, Publication date: Jan. 26, 1995, Abstract, 1 page.
DE 4326906, Publication date: Feb. 16, 1995, Abstract, 1 page.
Patent Cooperation Treaty, International Searching Authority, Search Report, PCT/US2013/074400, Date of mailing: Feb. 17, 2014, 4 pages.
Patent Cooperation Treaty, International Searching Authority, Written Opinion, PCT/US2013/074400, Date of mailing: Feb. 17, 2014, 4 pages.
Patent Cooperation Treaty, International Searching Authority, Search Report, PCT/US2013/074403, Date of mailing: Feb. 18, 2014, 5 pages.
Patent Cooperation Treaty, International Searching Authority, Search Report, PCT/US2013/074617, Date of mailing: Feb. 13, 2014, 4 pages.
Patent Cooperation Treaty, International Searching Authority, Written Opinion, PCT/US2013/074403; Date of mailing: Feb. 18, 2014, 7 pages.
Patent Cooperation Treaty, International Searching Authority, PCT/US2013/074617, Written Opinion, Date of mailing: Feb. 13, 2014, 5 pages.

*Primary Examiner* — Terressa Boykin
(74) *Attorney, Agent, or Firm* — Cantor Colburn LLP

(57) ABSTRACT

The disclosure provides a method for alcoholysis of a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene. The method comprises contacting the composition with a solvent that forms a solution or a filterable suspension of the component but not the polycarbonate; separating the solution or the filterable suspension from the polycarbonate; and heating the polycarbonate in the presence of an alcohol and a catalyst at a temperature from 70° C. to 200° C., and a pressure from 5 mbar to 40 bar for a time sufficient to depolymerize the polycarbonate and produce a dihydroxy aromatic compound and a dialkyl carbonate.

36 Claims, No Drawings

METHOD FOR ALCOHOLYSIS OF POLYCARBONATE COMPOSITIONS CONTAINING FLAME RETARDANT OR ACRYLONITRILE-BUTADIENE-STYRENE

BACKGROUND

This disclosure is directed to methods for the alcoholysis of polycarbonate compositions containing flame retardants or acrylonitrile-butadiene-styrene, and in particular to methods of making bisphenol A by methanolysis of a bisphenol A polycarbonate composition containing phosphorus-containing flame retardants or acrylonitrile-butadiene-styrene.

Polycarbonates are useful in the manufacture of articles and components for a wide range of applications, from automotive parts to electronic appliances. However, polycarbonates are not biodegradable and can present a significant bulk waste disposal problem. Accordingly, efforts have been made to recover valuable resources from polycarbonate wastes.

Polycarbonates can depolymerize in the presence of a catalyst to generate monomers such as bisphenol A and dimethyl carbonate. However, it is challenging to depolymerize polycarbonates in wastes, particularly, post-consumer low purity wastes, since these wastes contain various chemicals in addition to polycarbonates. These various chemicals can poison the catalyst, contaminate the products, and render the process expensive and inefficient. Thus, a cost effective process that allows the recovery of valuable high quality products from polycarbonate wastes is continuously sought.

BRIEF DESCRIPTION

The disclosure provides a method for alcoholysis of a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene. The method comprises contacting the composition with a solvent that forms a solution or a filterable suspension of the component but not the polycarbonate; separating the solution or the filterable suspension from the polycarbonate; and heating the separated polycarbonate in the presence of an alcohol and a catalyst at a temperature from 70° C. to 200° C., and a pressure from 5 mbar to 40 bar for a time sufficient to depolymerize the polycarbonate to provide a dihydroxy aromatic compound and a dialkyl carbonate.

Alternatively, the method comprises contacting the polycarbonate-containing composition with a solvent that forms a solution of the polycarbonate but not the component; separating the solution from the component; recovering the polycarbonate from the solution; and heating the recovered polycarbonate in the presence of an alcohol and a catalyst at a temperature from 70° C. to 200° C., and a pressure from 5 mbar to 40 bar for a time sufficient to depolymerize the polycarbonate to provide a dihydroxy aromatic compound and a dialkyl carbonate.

The disclosure also provides a method to separate a component from a polycarbonate, wherein the component is a phosphorus-containing flame retardant, acrylonitrile-butadiene-styrene, or a combination of the phosphorus-containing flame retardant and acrylonitrile-butadiene-styrene. The method comprises contacting a mixture comprising the component and the polycarbonate with a solvent that forms a solution or filterable suspension of the component but not the polycarbonate; and separating the solution or suspension from the polycarbonate.

Alternatively, the method comprises contacting the mixture comprising the component and the polycarbonate with a solvent that forms a solution of the polycarbonate but not the component; and separating the solution from the component.

The disclosure further provides a method to separate a phosphorus-containing flame retardant, acrylonitrile-butadiene-styrene, and a polycarbonate. The method comprises contacting a mixture comprising a phosphorus-containing flame retardant, acrylonitrile-butadiene-styrene and a polycarbonate with a first solvent which selectively dissolves the flame retardant and forms a filterable suspension of acrylonitrile-butadiene-styrene but not the polycarbonate; separating the solubilized flame retardant and filterable acrylonitrile-butadiene-styrene as a mixture from the polycarbonate; removing the first solvent from the mixture to provide a solid containing the flame retardant and the acrylonitrile-butadiene-styrene; contacting the solid with a second solvent which selectively dissolves the flame retardant, but not acrylonitrile-butadiene-styrene; and separating the dissolved flame retardant from acrylonitrile-butadiene-styrene.

A method for the manufacture of a polycarbonate comprises contacting a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene with a solvent that forms a solution or a filterable suspension of the component but not the polycarbonate; separating the solution or suspension from the polycarbonate; heating the separated polycarbonate in the presence of an alcohol and a catalyst at a temperature from 70° C. to 200° C., and a pressure from 5 mbar to 40 bar for a time sufficient to depolymerize the polycarbonate to provide a dihydroxy aromatic compound and a dialkyl carbonate; recovering the dihydroxy aromatic compound; and polymerizing the dihydroxy aromatic compound and a carbonyl source to provide the polycarbonate.

A method for the manufacture of a polycarbonate comprises contacting a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene with a solvent which forms a solution of the polycarbonate but not the component; separating the solution from the component; recovering the polycarbonate from the solution; and heating the recovered polycarbonate in the presence of an alcohol and a catalyst at a temperature from 70° C. to 200° C., and a pressure from 5 mbar to 40 bar for a time sufficient to depolymerize the polycarbonate to provide a dihydroxy aromatic compound and a dialkyl carbonate; recovering the dihydroxy aromatic compound; and polymerizing the dihydroxy aromatic compound and a carbonyl source to provide the polycarbonate.

A method for the manufacture of diphenyl carbonate comprises contacting a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene with a solvent which forms a solution or a filterable suspension of the component but not the polycarbonate; separating the solution or suspension from the polycarbonate; heating the polycarbonate in the presence of an alcohol and a catalyst at a temperature from 70° C. to 200° C., and a pressure from 5 mbar to 40 bar for a time sufficient to depolymerize the polycarbonate and produce a dihydroxy aromatic compound and a dialkyl carbonate; recovering the dialkyl carbonate; and reacting the dialkyl carbonate with phenol to provide diphenyl carbonate.

A method for the manufacture of diphenyl carbonate also comprises contacting a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene with a solvent that forms a solution of the polycarbonate but not the component; separating the solution from the component; recovering the polycarbonate from the solution; and heating the recovered polycarbonate in the presence of an alcohol and a catalyst at a temperature from 70° C. to 200° C., and a pressure from 5 mbar to 40 bar for a time sufficient to depolymerize the polycarbonate and produce a dihydroxy aromatic compound and a dialkyl carbonate; recovering the dialkyl carbonate; and reacting the dialkyl carbonate with phenol to provide diphenyl carbonate.

Alternatively, a method for the manufacture of a polycarbonate comprises contacting a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene with a solvent which forms a solution or a filterable suspension of the component but not the polycarbonate; separating the solution or suspension from the polycarbonate; heating the polycarbonate in the presence of an alcohol and a catalyst at a temperature from 70° C. to 200° C., and a pressure from 5 mbar to 40 bar for a time sufficient to depolymerize the polycarbonate and produce a dihydroxy aromatic compound and a dialkyl carbonate; recovering the dihydroxy aromatic compound and the dialkyl carbonate; reacting the dialkyl carbonate with phenol to provide diphenyl carbonate; and polymerizing the dihydroxy aromatic compound and diphenyl carbonate to provide the polycarbonate.

A method for the manufacture of a polycarbonate can also comprise contacting a polycarbonate-containing composition comprising a polycarbonate and a component comprising a phosphorus-containing flame retardant, an acrylonitrile-butadiene-styrene, or a combination of the phosphorus-containing flame retardant and acrylonitrile-butadiene-styrene with a solvent that forms a solution of polycarbonate but not the component; separating the solution from the component; recovering the polycarbonate from the solution; and heating the recovered polycarbonate in the presence of an alcohol and a catalyst at a temperature from 70° C. to 200° C., and a pressure from 5 mbar to 40 bar for a time sufficient to depolymerize the polycarbonate and produce a dihydroxy aromatic compound and a dialkyl carbonate; recovering the dihydroxy aromatic compound and the dialkyl carbonate; reacting the dialkyl carbonate with phenol to provide diphenyl carbonate; and polymerizing the dihydroxy aromatic compound and diphenyl carbonate to provide the polycarbonate.

The disclosure also provides polycarbonates manufactured by the above described methods.

These and other non-limiting characteristics are more particularly described below.

DETAILED DESCRIPTION

Polycarbonate-containing compositions obtained from wastes can comprise flame retardants or acrylonitrile-butadiene-styrene (ABS). The presence of flame retardants sometimes requires the use of large amounts of catalyst for depolymerization of polycarbonate. ABS, on the other hand, coats the surfaces of the reactor requiring expensive cleaning of the reactor. Accordingly, recycling a polycarbonate composition containing flame retardants or ABS can be less efficient than desirable. Surprisingly, the treatment of the polycarbonate-containing compositions with an appropriate solvent has been found to effectively remove the phosphorus-containing flame retardant or ABS. This allows for complete depolymerization of the polycarbonate, even from compositions that contain a phosphorus-containing flame retardant or ABS. The ability to effectively remove a phosphorus-containing flame retardant or ABS and to carry out the alcoholysis reaction of the remaining polycarbonate-containing material is important to enable recycling of low-value polycarbonate-containing materials as these materials typically contain flame retardants or ABS.

Illustrative examples of solvents include acetone, ethyl acetate, methyl ethyl ketone, acetonitrile, or a combination comprising at least one of the foregoing. Solvents can also include other polar aprotic solvents. Polar aprotic solvents are solvents which display a molecular asymmetry but do not have a hydrogen attached to a strongly electronegative molecule and therefore do not contain a dissociable proton ($H^+$). The solvent dissolves the flame retardants or forms a filterable suspension of ABS but not the polycarbonate, that is, the ABS passes through the filter but not the polycarbonate. Accordingly, polycarbonate can be separated from the solution or filterable suspension that contains flame retardants or ABS. As used herein, "filterable suspension" refers to a suspension comprising particles of such a size that the particles can pass through certain filters, for example a filter having a pore size of 25 micrometers or less, for example 20 to 25 micrometers, such as Whatman 41 filters. In the case where the component comprises both flame retardants and ABS, the addition of the solvent to the polycarbonate-containing composition forms a filterable suspension comprising dissolved flame retardants, ABS particles that can pass through filters and polycarbonate that is neither soluble nor filterable, and thus cannot pass through filters.

If desired, the polycarbonate-containing composition can be treated with a solvent at an elevated temperature for a sufficient time to dissolve the flame retardants or form a filterable suspension of ABS. After the insoluble polycarbonate is removed, the extract can be distilled to remove the solvent. In the instance where the remaining solid contains both a flame retardant and ABS, a second solvent, such as an alcohol, can be added to selectively dissolve the flame retardant but not ABS. The dissolved flame retardant can subsequently be separated from insoluble ABS.

In another embodiment, the treatment of the polycarbonate-containing compositions with an appropriate solvent has been found to effectively dissolve the polycarbonate but not the phosphorus-containing flame retardant and ABS. The solvent used can be trichloromethane. Once the solution is separated from the phosphorus-containing flame retardant or ABS, polycarbonate can be recovered from the solution. For example, polycarbonate can be recovered by at least partially removing trichloromethane or adding a precipitating solvent such as methanol to the solution to reprecipitate the polycarbonate.

As used herein, a "polycarbonate" means compositions having repeating structural carbonate units of formula (1)

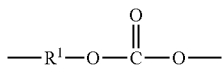
(1)

in which at least 60 percent of the total number of $R^1$ groups contain aromatic moieties and the balance thereof are aliphatic, alicyclic, or aromatic. In an embodiment, each $R^1$ is a $C_{6-30}$ aromatic group, that is, contains at least one aromatic moiety. $R^1$ can be derived from a dihydroxy compound of the formula HO—$R^1$—OH, in particular of formula (2)

$$HO\text{-}A^1\text{-}Y^1\text{-}A^2\text{-}OH \quad (2)$$

wherein each of $A^1$ and $A^2$ is a monocyclic divalent aromatic group and $Y^1$ is a single bond or a bridging group having one or more atoms that separate $A^1$ from $A^2$. In an embodiment, one atom separates $A^1$ from $A^2$. Specifically, each $R^1$ can be derived from a dihydroxy aromatic compound of formula (3)

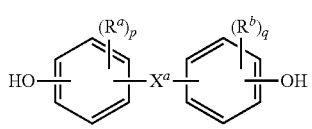
(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group. In an embodiment, the bridging group $X^a$ is single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. In an embodiment, p and q is each 1, and $R^a$ and $R^b$ are each a $C_{1-3}$ alkyl group, specifically methyl, disposed meta to the hydroxy group on each arylene group.

In an embodiment, $X^a$ is a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

In another embodiment, $X^a$ is a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

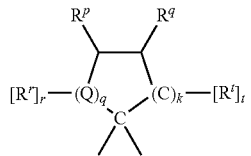
(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is 1 and i is 0, the ring as shown in formula (4) contains 4 carbon atoms, when k is 2, the ring as shown in formula (4) contains 5 carbon atoms, and when k is 3, the ring contains 6 carbon atoms. In an embodiment, two adjacent groups (e.g., $R^q$ and $R^t$ taken together) form an aromatic group, and in another embodiment, $R^q$ and $R^t$ taken together form one aromatic group and $R^r$ and $R^p$ taken together form a second aromatic group. When $R^q$ and $R^t$ taken together form an aromatic group, $R^p$ can be a double-bonded oxygen atom, i.e., a ketone.

"Polycarbonates" includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates or copolycarbonates.

Polycarbonate-containing compositions can come from various sources. Polycarbonate compositions containing flame retardants are also referred to as "FR polycarbonate" herein. FR polycarbonates are used in various components and housings in electronic devices. Once the devices are discarded, plastics are separated from metal and glass components and are processed to provide potential feedstocks for industrial use. These feedstocks are referred to as plastics from e-waste. Examples of FR polycarbonate-containing e-waste include plastics from float sink e-waste and trommel e-waste.

"Float sink e-waste" plastics are obtained via a liquid separation process. After being ground, e-waste materials are separated according to their relative buoyancy in selected liquids in a float sink tank. For example, in such processes a first float/sink tank is filled with plain water. Polyethylene and polypropylene float and are removed from polystyrene, acrylonitrile-butadiene-styrene (ABS), and FR polycarbonate, which sink. These "sinks" go into a second tank containing an aqueous solution of 1.035 g/cc density, as well as three rotating drums with paddle vanes. Polystyrene floats in this tank, while ABS and FR polycarbonate sink. The FR polycarbonate and ABS are a compatible blend, which processors sell as float sink e-waste plastics. Float sink e-waste plastics can be obtained, for example, from Global Electric and Electronic Processing (GEEP).

"Trommel e-waste" plastics are plastics from e-waste that have been ground and physically sorted via trommel screening. Trommel e-waste plastics are available, for example, from Global Electric and Electronic Processing (GEEP).

Other e-waste materials are first separated by hand prior to size reduction. Those parts believed to be primarily polycarbonate/ABS blends are then hand-picked and used as feedstocks for recycling. Such e-waste plastics are available from Recycletronics.

The phosphorus-containing flame retardants in the polycarbonate-containing composition include organic phosphates and organic compounds containing phosphorus-nitrogen bonds.

One type of organic phosphate is an aromatic phosphate of the formula $(GO)_3P{=}O$, wherein each G is independently an alkyl, cycloalkyl, aryl, alkylaryl, or aralkyl group, provided that at least one G is an aromatic group. Two of the G groups can be joined together to provide a cyclic group, for example, diphenyl pentaerythritol diphosphate. Aromatic phosphates include, phenyl bis(dodecyl) phosphate, phenyl bis(neopentyl) phosphite, phenyl bis(3,5,5'-trimethylhexyl) phosphate, ethyl diphenyl phosphate, 2-ethylhexyl di(p-tolyl) phosphate, bis(2-ethylhexyl) p-tolyl phosphate, tritolyl phosphate, bis(2-ethylhexyl)phenyl phosphate, tri(nonylphenyl) phosphate, bis(dodecyl) p-tolyl phosphate, dibutyl phenyl phosphate, 2-chloroethyl diphenyl phosphate, p-tolyl bis(2,5,5'-trimethylhexyl) phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulae below

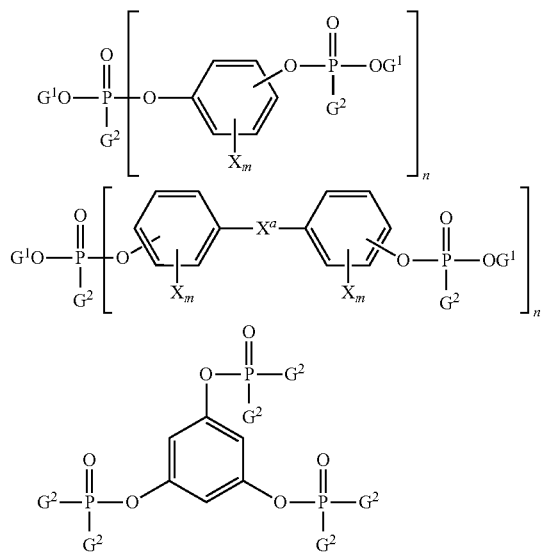

wherein each $G^1$ is independently a hydrocarbon having 1 to 30 carbon atoms; each $G^2$ is independently a hydrocarbon or hydrocarbonoxy having 1 to 30 carbon atoms; each X is independently a bromine or chlorine; m is 0 to 4, and n is 1 to 30. Di- or polyfunctional aromatic phosphorus-containing compounds include resorcinol tetraphenyl diphosphate (RDP), the bis(diphenyl) phosphate of hydroquinone and the bis(diphenyl) phosphate of bisphenol A, respectively, their oligomeric and polymeric counterparts, and the like.

Exemplary flame retardant compounds containing phosphorus-nitrogen bonds include phosphonitrilic chloride, phosphorus ester amides, phosphoric acid amides, phosphonic acid amides, phosphinic acid amides, tris(aziridinyl) phosphine oxide. The organic phosphorus-containing flame retardants are generally present in amounts of about 0.1 to about 20 parts by weight, for example, about 2 to about 18 parts by weight or about 4 to about 16 parts by weight, optionally about 2 to about 15 parts by weight, based on 100 parts by weight of the total composition, exclusive of any filler.

Polycarbonates in the FR polycarbonate compositions can be depolymerized by alcoholysis. As used herein, alcoholysis refers to a process that depolymerizes polycarbonate to produce dihydroxy aromatic compounds and dialkyl carbonates by using an alcohol as both a solvent and a reactant.

The alcohol can be a $C_{1-10}$ alcohol, for example, an alkyl alcohol such as methanol, ethanol, propanol, n-butanol, and an aryl alcohol such as phenol, cresols, and the like. Alcoholysis in the presence of an alkyl alcohol produces a dialkyl carbonate. Alcoholysis in the presence of an aryl alcohol produces a diaryl carbonate. Where the discussion and the examples herein refer to dialkyl carbonate, it is appreciated that alcoholysis processes to produce diaryl carbonate, and the use of recovered diaryl carbonate to prepare polycarbonates are also within the scope of the disclosure. When methanol is used, the alcoholysis is referred to as methanolysis, when ethanol is used, the process is referred to as ethanolyis, and so forth. Where the discussion and the examples herein refer to methanolysis, the skilled artisan will understand that other alcohols can be interchangeably used for what would generally be referred to as alcoholysis and that the latter is within the scope of the invention.

The catalyst, e.g., a transesterification catalyst, can be one or more of titanium isopropoxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, a zinc compound or a zirconium compound.

The hydroxide of an alkali metal or an alkaline earth metal can be lithium hydroxide, sodium hydroxide, potassium hydroxide, or calcium hydroxide. The quaternary ammonium salts of boron hydride and of aluminum hydride can be lithium aluminum hydride, sodium boron hydride and tetramethyl ammonium boron hydride. The hydrides of an alkali metal and of an alkaline earth metal can be lithium hydride, sodium hydride or calcium hydride. The alkoxides of an alkali metal and of an alkaline earth metal can be lithium methoxide, sodium ethoxide or calcium methoxide. The aryloxides of an alkali metal and of an alkaline earth metal can be lithium phenoxide, sodium phenoxide, magnesium phenoxide, LiO—Ar—OLi, wherein Ar represents an arylene group, and NaO—Ar—ONa, wherein Ar represents an arylene group. The organic salts of an alkali metal and of an alkaline earth metal can be lithium acetate, calcium acetate, or sodium benzoate. The zinc compounds can be zinc oxide, zinc acetate or zinc phenoxide. The boron compounds can be boron oxide, boric acid, sodium borate, trimethyl borate, tributyl borate, triphenyl borate, ammonium borate, or phosphonium borate. The silicon compounds can be silicon oxide, sodium silicate, tetraalkylsilicon, tetraarylsilicon, or diphenyl-ethyl-ethoxysilicon. The germanium compounds can be germanium oxide, germanium tetrachloride, and germanium ethoxide or germanium phenoxide. The tin compounds can be tin oxide, dialkyltin oxide, dibutyltin oxide, dialkyltin carboxylate, or tin acetate. The tin compounds that have an alkoxy group or an aryloxy group bonded to tin can include ethyltin tributoxide and organotin compounds. Lead compounds include lead oxide, lead acetate, lead carbonate, and basic lead carbonate. Alkoxides and aryloxides of lead can also be used as a metal transesterification catalyst. One example of an aryloxide of lead is lead diphenoxide. Onium compounds can include quaternary ammonium salt, quaternary phosphonium salt, or a quaternary arsonium salt. The antimony compounds can include antimony oxide and antimony acetate. The manganese compounds can include manganese acetate, manganese carbonate and manganese borate. The titanium compounds include titanium oxide and titanium alkoxides and titanium aryloxide. The zirconium compounds include zirconium acetate, zirconium oxide, zirconium alkoxide, zirconium aryloxide, and zirconium acetylacetonate.

In addition to the foregoing, transesterification catalysts used herein can include tetrabutylammonium hydroxide, methyltributylammonium hydroxide, tetrabutylammonium acetate, tetrabutylphosphonium hydroxide, tetrabutylphosphonium acetate, or tetrabutylphosphonium phenolate. The transesterification catalyst as used herein can be one or more of the foregoing compounds. In specific embodiments, the catalyst is tetra(isopropyl)titanate, aluminum isopropoxide, dibutyltin oxide, metal phenoxides, or a combination containing at least one of the foregoing. Advantageously, the catalyst is a catalyst purge stream from a diphenyl carbonate production unit.

When the catalyst is a titanium-based catalyst, the catalyst can be removed by adding a sufficient amount of water to a blend of dihydroxy aromatic compound, the dialkyl compound and the alcohol to convert the catalyst to titanium dioxide, which can be filtered off.

A catalytically active amount of the catalyst can be less than 4 wt. %, 3 wt. %, 2 wt. %, 1 wt. %, 0.5 wt. %, 0.25 wt. %, 0.1 wt. %, 0.05 wt. %, 0.025 wt. %, 0.01 wt. % based on the total weight of the polycarbonate-containing composition and the alcohol. In specific embodiments, the catalyst can be present in an amount of 0.01 wt. % to 2 wt. %, 0.01 wt. % to 1 wt. %, or 0.01 wt. % to 0.1 wt. % based upon the total weight of the polycarbonate-containing composition and the alcohol.

The alcoholysis of polycarbonate is generally conducted at a temperature of at least 30° C., specifically a temperature from 70° C. to 200° C., more specifically 100° to 180° C., most specifically 130° to 170° C. At temperatures below 30° C., reaction rates can be too slow for economical operation. Atmospheric or super-atmospheric pressures can be used, for example up to 40 bar, specifically from 50 mbar to 40 bar, more specifically from 5 bar to 20 bar autogenous pressure.

The alcoholysis of polycarbonate can be conducted for about 0.5 to about 10 hours, specifically about 1 to about 5 hours, more specifically about 2 to about 4 hours depending on the temperature and pressure and the specific polycarbonate-containing composition and catalyst used. Advantageously, the conversion of the polycarbonate is 99% complete in less than 4 hours.

A weight ratio of alcohol to polycarbonate-containing composition of 1:1 to 10:1, specifically 2:1 to 8:1, more specifically 2:1 to 6:1 can be used. A molar ratio of alcohol such as methanol, ethanol, or butanol to polycarbonate-containing composition can be 8:1 to 80:1, specifically 16:1 to 64:1, more specifically 16:1 to 48:1, While other ratios than those set out herein can be used, an excess of alcohol can be desirable as it is used both as a reagent and a solvent.

The combination of the alcohol and the dialkyl carbonate can be separated from the dihydroxy aromatic compound by distillation. The alcohol/dialkyl carbonate stream, which contains up to 50 wt. % of dialkyl carbonate, can be reused for alcoholysis of polycarbonates. Alternatively, the alcohol/dialkyl carbonate mixture can be separated into an alcohol rich substream and a dialkyl carbonate rich substream with each substream containing greater than 75% of alcohol or dialkyl carbonate. The alcohol rich substream can be reused to depolymerize polycarbonates. In an embodiment, one or both of the substreams can be purified before use in further reactions.

Illustrative examples of dialkyl carbonates include dimethyl carbonate (DMC), diethyl carbonate, and dibutyl carbonate. Some illustrative examples of specific dihydroxy aromatic compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl) cyclopentane, 1,1-bis(4-hydroxyphenyl)cyclohexane, 1,1-bis(4-hydroxyphenyl)isobutene, 1,1-bis(4-hydroxyphenyl) cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl) propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Other specific examples of dihydroxy aromatic compounds include 1,1-bis(4-hydroxyphenyl)methane, 1,1-bis(4-hydroxyphenyl)ethane, 2,2-bis(4-hydroxyphenyl) propane (also referred to as "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, 2-phenyl-3,3-bis(4-hydroxyphenyl) phthalimidine (PPPBP), 1,1-bis(4-hydroxy-3-methylphenyl)cyclohexane (DMBPC), and 1,4:3,6-dianhydro-D-sorbitol. In one specific embodiment, the dihydroxy aromatic compound derived from the alcoholysis of polycarbonate is bisphenol A.

The obtained dihydroxy aromatic compound can be sold as is or used in further reactions including polymerization to make polycarbonate. The obtained dialkyl carbonate can react with phenol to provide diphenyl carbonate. In an embodiment, the dihydroxy aromatic compound and the dialkyl carbonate can be purified before used for further reactions.

For example, the dihydroxy aromatic compound can be used to form a polycarbonate by polymerization with a carbonyl source, i.e., a carbonate precursor. Polymerization of the dihydroxy aromatic compound to produce a polycarbonate can be by interfacial or melt polymerization methods. Although the reaction conditions for interfacial polymerization can vary, the process generally involves dissolving or dispersing a dihydroxy aromatic compound in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., 8 to 12. The most commonly used water immiscible solvents include methylene chloride, 1,2-dichloroethane, chlorobenzene, toluene, and the like.

Carbonate precursors include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an embodiment, an interfacial polymerization reaction to form carbonate linkages uses phosgene as a carbonate precursor, and is referred to as a phosgenation reaction.

Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cl^-$, $Br^-$, a $C_{1-8}$ alkoxy group or a $C_{6-18}$ aryloxy group. An effective amount of a phase transfer catalyst can be 0.1 to 10 wt. % based on the weight of bisphenol in the phosgenation mixture. In another embodiment an effective amount of phase transfer catalyst can be 0.5 to 2 wt. % based on the weight of bisphenol in the phosgenation mixture.

Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate.

Alternatively, melt processes can be used to make the polycarbonates. Melt polymerization may be conducted as a batch process or as a continuous process. In either case, the melt polymerization conditions used may comprise two or more distinct reaction stages, for example, a first reaction stage in which the starting dihydroxy aromatic compound and diaryl carbonate are converted into an oligomeric polycarbonate and a second reaction stage wherein the oligomeric polycarbonate formed in the first reaction stage is converted to high molecular weight polycarbonate. Such "staged" polymerization reaction conditions are especially suitable for use in continuous polymerization systems wherein the starting monomers are oligomerized in a first reaction vessel and the oligomeric polycarbonate formed therein is continuously transferred to one or more downstream reactors in which the oligomeric polycarbonate is converted to high molecular weight polycarbonate. Typically, in the oligomerization stage the oligomeric polycarbonate produced has a number average molecular weight of about 1,000 to about 7,500 Daltons. In one or more subsequent polymerization stages the number average molecular weight (Mn) of the polycarbonate is increased to between about 8,000 and about 25,000 Daltons (using polycarbonate standard).

The term "melt polymerization conditions" is understood to mean those conditions necessary to effect reaction between a dihydroxy aromatic compound and a diaryl carbonate in the presence of a transesterification catalyst. Typically, solvents are not used in the process, and the reactants dihydroxy aromatic compound and the diaryl carbonate are in a molten state. The reaction temperature can be about 100° C. to about 350° C., specifically about 180° C. to about 310° C. The pressure may be at atmospheric pressure, supra-atmospheric pressure, or a range of pressures from atmospheric pressure to about 15 torr in the initial stages of the reaction, and at a reduced pressure at later stages, for example about 0.2 to about 15 torr. The reaction time is generally about 0.1 hours to about 10 hours.

Catalysts used in the melt transesterification polymerization production of polycarbonates can include alpha or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other possible sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alpha transesterification catalysts include alkali or alkaline earth metal salts of a non-volatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising at least one of any of the foregoing catalysts can be used.

Possible beta catalysts can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used. The quaternary phosphonium compound can be a compound of the structure $(R^5)_4P^+X^-$, wherein each $R^5$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Where $X^-$ is a polyvalent anion such as carbonate or sulfate it is understood that the positive and negative charges in the quaternary ammonium and phosphonium structures are properly balanced. For example, where $R^{20}$-$R^{23}$ are each methyl groups and $X^-$ is carbonate, it is understood that $X^-$ represents $2(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of alpha and beta catalyst used can be based upon the total number of moles of dihydroxy compound used in the polymerization reaction. When referring to the ratio of beta catalyst, for example, a phosphonium salt, to all dihydroxy compounds used in the polymerization reaction, it is convenient to refer to moles of phosphonium salt per mole of the dihydroxy compound, meaning the number of moles of phosphonium salt divided by the sum of the moles of each individual dihydroxy compound present in the reaction mixture. The alpha catalyst can be used in an amount sufficient to provide $1 \times 10^{-2}$ to $1 \times 10^{-8}$ moles, specifically, $1 \times 10^{-4}$ to $1 \times 10^{-7}$ moles of metal per mole of the dihydroxy compounds used. The amount of beta catalyst (e.g., organic ammonium or phosphonium salts) can be $1 \times 10^{-2}$ to $1 \times 10^{-5}$, specifically $1 \times 10^{-3}$ to $1 \times 10^{-4}$ moles per total mole of the dihydroxy compounds in the reaction mixture.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of 0.05 to 2.0 weight %. Mixtures comprising linear polycarbonates and branched polycarbonates can be used. The content of the following branching structures is 2,000 ppm or below.

The various embodiments are further illustrated by the following non-limiting examples.

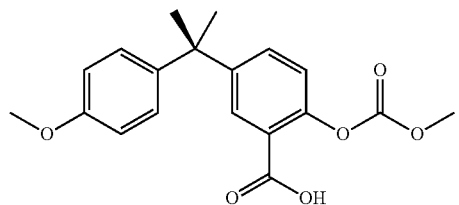

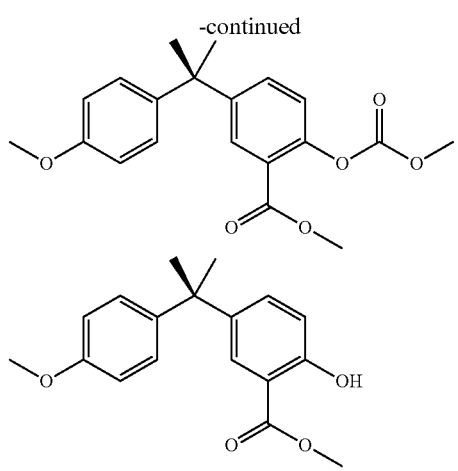

EXAMPLES

The materials used in the Examples or produced by the processes of the Examples are described in Table 1.

TABLE 1

| Component | Description | Source |
|---|---|---|
| Polycarbonate Feedstock #1 | A polycarbonate feedstock containing about 70 wt. % of bisphenol A polycarbonate; about 17 wt. % of acrylonitrile-butadiene-styrene resin; and about 11 wt. % of bisphenol A bis(diphenyl phosphate). | SABIC Innovative Plastics |
| Polycarbonate Feedstock #2 Recycle Grade (e-waste) | Polymer blends recovered from electronic devices containing about 70 wt. % of polycarbonates as determined by IR | Recycletronics |
| Polycarbonate Feedstock #3 Recycle Grade (float sink e-waste) | Recycle grade e-waste that has been ground and physically sorted via float sink screening containing about 12 wt. % of polycarbonates as determined by IR | Global Electric and Electronic Processing |
| Ti-isopropoxide (TPT) | Tetra(isopropyl)titanate | Sigma Aldrich |
| Methanol | | Merck |
| BPA | 4,4'-(propane-2,2-diyl)diphenol | Alcoholysis product |
| DMC | Dimethyl carbonate | Alcoholysis product |

General Procedures

All methanolysis studies were conducted in 2 liter (titanium) Amar High Pressure Reactor equipped with a heating jacket with a jacket oil heater and a cooling coil with cooling water tank. The reactor was also equipped with a bottom discharge valve to take out the reaction mass. The reactor was flushed several times with pressurized nitrogen, prior to commencement of each experiment, thereby ensuring an oxygen free atmosphere inside the reactor. Then the reactor was charged with desired quantities of methanol, polycarbonate waste, and catalyst. The reactor was again flushed several times with pressurized nitrogen. This also ensured zero leak conditions of the system. The speed of agitation was then adjusted to the desired value. The reactor contents were heated to the desired temperature by circulating hot oil through the reactor jacket. The temperature of the reactor was controlled within ±0.5° C. of the set temperature by circulating cold water through the cooling coil. Once the desired temperature was reached the time was noted as time zero. The entire system was thus operated in a batch mode for 180 min. At the end of the experiment, the reactor contents were cooled to 25°-30° C. by circulating cooling water through cooling coil. The reactor was then depressurized to atmospheric pressure manually by opening the vent valve and the reactor contents were drained by using bottom drain valve. The reaction mixture was then filtered and distilled to recover methanol and DMC. The solid left behind was analyzed for BPA purity by High Pressure Liquid Chromatography (HPLC). DMC obtained during distillation was analyzed by Gas Chromatography (GC).

Polycarbonate content was quantified by Infrared Radiation spectroscopy (IR). BPA was quantified by HPLC, and DMC was quantified by GC.

Example 1

140 grams of polycarbonate feedstock #1 was contacted with 0.7 liters of acetone at a temperature of 50° C. After holding for 300 minutes, the acetone extract and dissolved components were separated from the insoluble polycarbonate (94% purity). The polycarbonate was treated with an excess of methanol and tetra(isopropyl)titanate to initiate methanolysis of the polycarbonate and produced bisphenol A (95% purity, 82% yield) and dimethyl carbonate (74% yield). The acetone extract was distilled to remove acetone, and the remaining solid was treated with methanol to dissolve bisphenol A bis(diphenylphosphate) thus separating it from insoluble Acrylonitrile-Butadiene-Styrene.

Example 2

140 grams of polycarbonate feedstock #2 (containing about 70% polycarbonate) was contacted with 0.7 liters of acetone at a temperature of 50° C. After holding for 300 minutes, the acetone extract and dissolved components were separated from the insoluble polycarbonate. The polycarbonate was treated with an excess of methanol and tetra(isopropyl)titanate to initiate methanolysis of the polycarbonate and produced bisphenol A (95% purity, 91% yield) and dimethyl carbonate (81% yield). The acetone extract was distilled to remove acetone, and the remaining solid was treated with methanol to dissolve bisphenol A bis(diphenylphosphate) thus separating it from the insoluble Acrylonitrile-Butadiene-Styrene.

Example 3

200 grams of polycarbonate feedstock #3 (containing about 12% polycarbonate) were contacted with 1.6 liters of trichloromethane at room temperature. After holding for 180 minutes, the trichloromethane extract and dissolved components were separated from the insoluble components and was reprecipitated with methanol. The methanol insoluble precipitate contained 138 g of polycarbonate. 100 g of this polycarbonate was treated with methanol and tetra(isopropyl) titanate to initiate methanolysis of the polycarbonate and produced bisphenol A (90% purity, 84% yield) and dimethyl carbonate (82% yield).

The singular forms "a," "an," and "the" include plural referents unless the context clearly dictates otherwise. "Or" means "and/or." Thus, reference to "compositions containing flame retardant or ABS," for example, means composition containing flame retardant, ABS, or both. The endpoints of all ranges directed to the same component or property are inclusive and independently combinable. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

As used herein, a "combination" is inclusive of blends, mixtures, alloys, reaction products, and the like. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-19}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylene-aryl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for alcoholysis of a polycarbonate-containing composition comprising a polycarbonate and a component comprising a phosphorus-containing flame retardant, acrylonitrile-butadiene-styrene, or a combination of the phosphorus-containing flame retardant and acrylonitrile-butadiene-styrene, the method comprising
    contacting the composition with a solvent that forms a solution or filterable suspension of the component but not the polycarbonate;
    separating the solution or suspension from the polycarbonate; and
    heating the separated polycarbonate with an alcohol in the presence of a catalyst at a temperature from 70° C. to 200° C., and a pressure from 5 mbar to 40 bar for a time sufficient to depolymerize the polycarbonate to provide a dihydroxy aromatic compound and a dialkyl carbonate.

2. The method of claim 1, wherein the polycarbonate is bisphenol A polycarbonate, and the dihydroxy aromatic compound is bisphenol A.

3. The method of claim 1, wherein the alcohol is methanol, ethanol, or n-butanol.

4. The method of claim 1, wherein the alcohol is added as a methanol stream containing from 0 to 50 weight percent of dimethyl carbonate.

5. The method of claim 1, wherein the dialkyl carbonate is dimethyl carbonate, diethyl carbonate or dibutyl carbonate.

6. The method of claim 1, wherein the phosphorus-containing flame retardant is bisphenol A bis(diphenyl phosphate), resorcinol bis(diphenyl phosphate) or a combination thereof.

7. The method of claim 1, wherein the solvent is a polar aprotic solvent.

8. The method of claim 1, wherein the solvent is acetone, ethyl acetate, methylethyl ketone, acetonitrile, or a combination comprising at least one of the foregoing.

9. The method of claim 1, wherein the solvent is acetone.

10. The method of claim 1, wherein the catalyst is a transesterification catalyst.

11. The method of claim 10, wherein the transesterification catalyst is a catalyst purge stream from a diphenyl carbonate production unit.

12. The method of claim 1, wherein the catalyst is present in an amount of 0.01 wt. % to 4 wt. % based on the total weight of the polycarbonate-containing composition and the alcohol.

13. The method of claim 1, wherein the alcohol is present in an amount of 2 times to 6 times of that of the polycarbonate-containing composition.

14. A method for alcoholysis of a polycarbonate-containing composition comprising a polycarbonate and a component comprising a phosphorus-containing flame retardant, acrylonitrile-butadiene-styrene, or a combination of the phosphorus-containing flame retardant and acrylonitrile-butadiene-styrene, the method comprising
    contacting the composition with a solvent that forms a solution of the polycarbonate but not the component;
    separating the solution from the component;
    recovering the polycarbonate from the solution; and
    heating the recovered polycarbonate in the presence of an alcohol and a catalyst at a temperature from 70° C. to 200° C., and a pressure from 5 mbar to 40 bar for a time sufficient to depolymerize the polycarbonate to provide a dihydroxy aromatic compound and a dialkyl carbonate.

15. The method of claim 14, wherein the solvent is trichloromethane.

16. A method to separate a component from a polycarbonate, wherein the component comprises a phosphorus-containing flame retardant, acrylonitrile-butadiene-styrene, or a combination of the phosphorus-containing flame retardant and acrylonitrile, the method comprising
    contacting a mixture comprising the component and the polycarbonate with a solvent that forms a solution or a filterable suspension of the component but not the polycarbonate; and
    separating the solution or filterable suspension from the polycarbonate.

17. The method of claim 16, wherein the phosphorus-containing flame retardant is bisphenol A bis(diphenyl phosphate), resorcinol bis(diphenyl phosphate) or a combination thereof.

18. The method of claim 16, wherein the solvent is a polar aprotic solvent.

19. The method claim 16, wherein the solvent is acetone, ethyl acetate, methylethyl ketone, acetonitrile, or a combination comprising at least one of the foregoing.

20. A method to separate a component from a polycarbonate, wherein the component comprises a phosphorus-containing flame retardant, acrylonitrile-butadiene-styrene, or a combination of the phosphorus-containing flame retardant and acrylonitrile, the method comprising
    contacting a mixture comprising the component and the polycarbonate with a solvent that forms a solution of the polycarbonate but not the component; and
    separating the solution from the polycarbonate.

21. The method of claim 20, wherein the solvent is trichloromethane.

22. A method to separate a phosphorus-containing flame retardant, acrylonitrile-butadiene-styrene, and a polycarbonate, comprising
    contacting a mixture comprising a phosphorus-containing flame retardant, acrylonitrile-butadiene-styrene and a polycarbonate with a first solvent that selectively dissolves the flame retardant and forms a filterable suspension of acrylonitrile-butadiene-styrene but not the polycarbonate;
    separating the solubilized flame retardant and the filterable acrylonitrile-butadiene-styrene as a mixture from the polycarbonate;
    removing the first solvent from the mixture to provide a solid containing the flame retardant and acrylonitrile-butadiene-styrene;
    contacting the solid with a second solvent which selectively dissolves the flame retardant, but not acrylonitrile-butadiene-styrene; and
    separating dissolved flame retardant from acrylonitrile-butadiene-styrene.

23. The method of claim 22, wherein the phosphorus-containing flame retardant is bisphenol A bis(diphenyl phosphate), resorcinol bis(diphenyl phosphate) or a combination thereof.

24. The method of claim 22, wherein the first solvent is a polar aprotic solvent.

25. The method of claim 22, wherein the first solvent is acetone, ethyl acetate, methylethyl ketone, acetonitrile, or a combination comprising at least one of the foregoing.

26. The method of claim 18, wherein the second solvent is an alcohol.

27. A method for the manufacture of a polycarbonate comprising
   recovering the dihydroxy aromatic compound of claim 1; and
   polymerizing the dihydroxy aromatic compound and a carbonyl source to provide the polycarbonate.

28. A method for the manufacture of a polycarbonate comprising
   recovering the dihydroxy aromatic compound of claim 14; and
   polymerizing the dihydroxy aromatic compound and a carbonyl source to provide the polycarbonate.

29. A method for the manufacture of diphenyl carbonate comprising
   recovering the dialkyl carbonate of claim 1; and
   reacting the dialkyl carbonate with phenol to provide diphenyl carbonate.

30. A method for the manufacture of diphenyl carbonate comprising
   recovering the dialkyl carbonate of claim 14; and
   reacting the dialkyl carbonate with phenol to provide diphenyl carbonate.

31. A method for the manufacture of a polycarbonate comprising
   recovering the dihydroxy aromatic compound and the dialkyl carbonate of claim 1;
   reacting the dialkyl carbonate with phenol to provide diphenyl carbonate; and
   polymerizing the dihydroxy aromatic compound and diphenyl carbonate to provide the polycarbonate.

32. A method for the manufacture of a polycarbonate comprising
   recovering the dihydroxy aromatic compound and the dialkyl carbonate of claim 14;
   reacting the dialkyl carbonate with phenol to provide diphenyl carbonate; and
   polymerizing the dihydroxy aromatic compound and diphenyl carbonate to provide the polycarbonate.

33. A polycarbonate manufactured by the method of claim 27.

34. A polycarbonate manufactured by the method of claim 28.

35. A polycarbonate manufactured by the method of claim 31.

36. A polycarbonate manufactured by the method of claim 32.

* * * * *